United States Patent [19]

Cantatore et al.

[11] Patent Number: 4,536,581

[45] Date of Patent: Aug. 20, 1985

[54] PROCESS FOR PREPARING 2,2,6,6-TETRAMETHYL-4-PIPERIDONE

[75] Inventors: Giuseppe Cantatore, Casalecchio di Reno; Paolo Cassandrini, Bologna, both of Italy

[73] Assignee: Ciba-Geigy S.p.A., Origgo, Italy

[21] Appl. No.: 495,713

[22] Filed: May 18, 1983

Related U.S. Application Data

[63] Continuation-in-part of Ser. No. 159,169, Jun. 13, 1980, abandoned, which is a continuation of Ser. No. 21,194, Mar. 16, 1979, abandoned.

[30] Foreign Application Priority Data

Mar. 31, 1978 [IT] Italy .................. 21858 A/78

[51] Int. Cl.$^3$ .......................................... C07D 211/74
[52] U.S. Cl. ................................................ 546/242
[58] Field of Search .................................... 546/242

[56] References Cited

U.S. PATENT DOCUMENTS 3,513,170 5/1970 Murayama et al. ................ 546/242

FOREIGN PATENT DOCUMENTS 520357 7/1976 U.S.S.R. .............................. 546/242

OTHER PUBLICATIONS

Sosnovsky, G., et al., *Synthesis*, 11, 735-6, (1976).
Sosnovsky, G., et al., *Z. Naturfursch, B: Anorg. Chem., Org. Chem.*, 32B, 328-37 and 338-46, (1977).

Primary Examiner—Richard A. Schwartz
Attorney, Agent, or Firm—Morgan, Finnegan, Pine, Foley & Lee

[57] ABSTRACT

A process for preparing 2,2,6,6-tetramethyl-4-piperidone from ammonia and acetone, wherein acetone and ammonia are reacted in a single stage for a time of 2 to 8 hours in an acetone:ammonia molar ratio of 20:1 to 4:1, at a temperature of 50° to 120° C. and at a pressure of 1 to 50 atmospheres, in the presence of 0.001–0.1 moles of acid catalysts per mole of acetone used in the reaction.

2 Claims, No Drawings

PROCESS FOR PREPARING 2,2,6,6-TETRAMETHYL-4-PIPERIDONE

The present application is a continuation-in-part application of Ser. No. 159,169 filed June 13, 1980, now abandoned, which in turn is a continuation of Ser. No. 021,194, filed Mar. 16, 1979, now abandoned.

This invention relates to a new process for preparing 2,2,6,6-tetramethyl-4-piperidone, commonly known as triacetonamine. More precisely, the present invention relates to a simple and economical industrial process for producing triacetonamine from acetone and ammonia.

Triacetonamine is a compound of formula

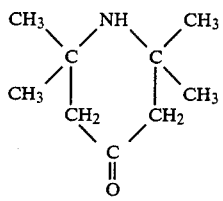

which is of considerable industrial importance as an intermediate in the preparation of stabilisers.

Because of the interest in this compound, various syntheses have been proposed for its preparation, but without any of them being able to be considered truly satisfactory on an industrial scale. In particular, various methods have been attempted for preparing triacetonamine from acetone and ammonia.

However, it has been found (U.S. Pat. No. 2,516,626) that by directly reacting acetone with anhydrous ammonia in the presence of an acid catalyst at a temperature of 25° to 35° C., instead of producing triacetonamine, 2,2,4,4,6-pentamethyl-tetrahydropyrimidine or acetonine is produced, of formula

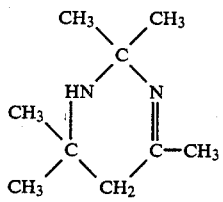

The reaction is carried out at a molar ratio of acetone-:ammonia of around 1.5:1, but the ratio of the reagents is considered not critical.

After purification, the acetonine thus produced can be reacted with a Lewis acid in the presence of water to give triacetonamine (U.S. Pat. No. 3,513,170).

However, such a two stage process is too complicated and costly to be advantageously applied on an industrial scale. On the other hand, the attempts made to carry out said process without separating the intermediate product have given unsatisfactory results, because complex mixtures of various products form from which it is difficult to separate triacetonamine with a satisfactory degree of purity.

More recently, another two stage process has been proposed for preparing triacetonamine from acetone and ammonia (U.S. Pat. No. 3,959,295).

This process consists essentially of:

a-reacting acetone with ammonia in a molar ratio of approximately 1:1 at a temperature of 5° to 35° C., in the presence of an acid catalyst b-completing the reaction by heating for several hours at a temperature of 50° to 55° C., possibly adding further acetone.

Again, the ratio of the reagents is not considered critical.

The main disadvantage of this process is the very long reaction time, which can vary from 20 to 30 hours according to the reaction conditions and the catalyst used.

Another Patent (Russian Pat. No. 520,357) describes the preparation of triacetonamine by reaction of acetone and ammonia at a temperature of 60°–80° C., for a time of 3–5 hours in the presence of $AlCl_3$ as the catalyst; this process, where a molar ratio acetone:ammonia comprised between 3:3 and 1:4 is used leads to triacetonamine with a yield which never exceeds about 30%.

The reaction between acetone and ammonia in the presence of $CaCl_2$ as catalyst was investigated by Sosnovsky et al (Synthesis, 11, 735-6 (1976); Z. Naturforsch. 1977, 32b, 328-337, 338-346). Under the best conditions identified by Sosnovsky, which include a maximum molar ratio acetone:ammonia of about 2:1, the reaction is completed only after seven days.

We have now quite unexpectedly found that there is a specific range of molar ratios acetone:ammonia, never considered nor suggested in the prior art, within which it is possible to produce triacetonamine with a high yield and a high degree of purity, in a single stage and in short time, i.e. in a industrially highly significant manner.

More precisely we have found a industrial process for the production of triacetonamine from acetone and ammonia consisting essentially of reacting acetone with ammonia in an acetone:ammonia molar ratio of 20:1 to 4:1 for a time of 1 to 12 hours at a temperature of 50° to 120° C., and at a pressure of 1 to 50 atmospheres in the presence of acid catalysts used in a quantity of 0.001 to 0.1 moles per mole of acetone.

Within these defined limits, the preferred conditions are: acetone:ammonia molar ratio of 10:1 to 4:1, temperature 60° to 100° C., pressure 1 to 5 atmospheres, quantity of acid catalyst 0.01 to 0.05 moles per mole of acetone, used, reaction time 2 to 8 hours.

Of particular importance is the fact that the new process reduces the formation of by-products to a minimum, and in particular products having a boiling point higher than the boiling point of triacetonamine, which besides hindering the obtaining of a high purity product cannot be recycled, thus making it impossible to totally convert the acetone into triacetonamine and representing a serious ecological problem.

As the process according to the present invention can be effected in a single stage in a short time, and at a moderate temperature and pressure, it can be carried out using very simple equipment, and from all points of view is extremely simple and economical when used on an industrial scale.

The reaction can be carried out using pure acetone, or acetone containing the acetone condensation products such as mesityl oxide, diacetone alcohol, diacetonamine, acetonine, forone, and triacetonediamine obtained as by-products of the previous reactions. In this manner it is possible to completely convert the acetone into triacetonamine with obvious economical advantages.

The reactions can also be carried out in the presence of inert organic solvents such as methanol, ethanol, isopropanol, n-butanol, benzol, toluol, xylol and cyclohexane.

The catalysts used are acid compounds such as Lewis acids, for example calcium chloride, zinc chloride, aluminium chloride, aluminium nitrate or boron trifluoride; organic or inorganic proton acids such as hydrochloric acid, hydrobromic acid, hydroiodic acid, sulphuric acid, nitric acid, phosphoric acid, perchloric acid, formic acid, acetic acid, chloroacetic acid, trichloroacetic acid, benzene sulphonic acid or para-toluene sulphonic acid; salts of said proton acids with ammonia, such as ammonium chloride, bromide, nitrate, acetate, trichloroacetate, paratoluenesulphonate, or salts of said proton acids with primary, secondary or tertiary aliphatic, cycloaliphatic, aromatic or heterocyclic amines such as methylamine, ethylamine, butylamine, dimethylamine, diethylamine, dibutylamine, trimethylamine, triethylamine, tributylamine, cyclohexylamine, aniline, morpholine, piperidine, pyridine, piperazine, ethylenediamine, hexamethylenediamine, diethylenetriamine, triethylenetetramine, tetraethylenepentamine or polyethyleneimines. In addition, anion exchange resins can be used, such as cross-linked polyamines salified with the aforementioned organic or inorganic proton acids. The catalysts can be used either singly or mixed.

In certain cases, it can be preferable to use mixtures of catalysts, such as mixtures of $CaCl_2$ or $ZnCl_2$ with proton acids or with ammonium salts of proton acids, such as a $CaCl_2$—$NH_4Cl$, $CaCl_2$—$NH_4NO_3$, $CaCl_2$—HCl or $ZnCl_2$—HCl mixture. The Ca or Zn salts aid separation of the water of reaction and simplify separation of the triacetonamine from the reaction mixture.

The triacetonamine can be isolated by known processes, for example by distillation, or by crystallisation in the form of the hydrate.

In some cases it is possible to directly use in subsequent reactions the crude triacetonamine obtained by simply distilling off the unreacted acetone and those reaction by-products which are more volatile than the triacetonamine.

The present invention will be better illustrated by some examples of preparation of triacetonamine according to the invention given hereinafter, these examples being purely illustrative and nonlimiting.

EXAMPLE 1

A mixture of 3500 g of acetone (60.3 moles), 440 g of granular $CaCl_2.2H_2O$ and 150 g of gaseous ammonia (8.81 moles) is heated to 80°–85° C. for six hours in an autoclave.

After this period, the hot aqueous layer is separated, the unreacted acetone is distilled from the organic layer, and the residue is cooled to 0° C. for four hours.

Crystalline triacetonamine hydrate is precipitated and is separated by filtration.

615 g of triacetonamine hydrate (M.P. 58°–60° C.) are obtained, equal to a yield of 72% of the converted acetone.

The same process was repeated by maintaining the described processing conditions, while using a molar ratio acetone:ammonia of 2:1, i.e. the maximum molar ratio suggested by above cited Sosnovsky.

Triacetonamine was obtained with a yield of 47% on the converted acetone.

EXAMPLE 2

A mixture of 3500 g of acetone (60.3 moles), 160 g of granular $CaCl_2.2H_2O$, 60 g of $NH_4Cl$ and 150 g of gaseous ammonia (8.8 moles) is heated to 80°–85° C. for six hours in an autoclave. After this period, the aqueous layer is separated, and the unreacted acetone and the overheads are distilled off.

The residue consists of 741 g of triacetonamine hydrate having a purity measured by gas chromatograph of 89.2% (yield with respect to converted acetone: 70%).

This product can be further purified or used as it is in many organic syntheses.

EXAMPLE 3

A mixture of 3500 g of acetone (60.3 moles), 160 g of granular calcium chloride bihydrate, 60 g of ammonium nitrate and 150 g of ammonia (8.8 moles) is heated in an autoclave for four hours at 80° C. The aqueous layer formed in the reaction is separated while hot, and the unreacted acetone is then removed from the organic layer by distillation.

The residue is cooled to 0° C. for four hours. 875 g of triacetonamine hydrate are obtained on filtration. Yield with respect to the converted acetone: 75%.

EXAMPLE 4

A mixture of 3500 g of acetone (60.3 moles) and 160 g of $Al(NO_3)_3 9H_2O$ is treated with 150 g of gaseous ammonia (8.8 moles) in an autoclave for four hours at 60° C. After separating the aqueous phase, the organic layer contains 795 g of triacetonamine which is separated by cooling as in Example 1.

Yield with respect to the converted acetone: 70%.

EXAMPLE 5

A mixture of 3500 g of acetone (60.3 moles), 150 g of zinc chloride and 50 cc of 37% hydrochloric acid is treated with 150 g of gaseous ammonia (8.8 moles) in an autoclave, with the temperature being kept at 70°–75° C. for four hours. The reaction mixture obtained contains 515 g of triacetonamine which can be separated as described in Example 1.

Yield with respect to the converted acetone: 68%.

EXAMPLE 6

A mixture of 5000 g of acetone (86.2 moles), 100 g of ammonium chloride and 200 g of gaseous ammonia (11.7 moles) is heated in an autoclave for five hours at 75°–80° C. The reaction mixture contains 1142 g of triacetonamine, which can be separated as described in Example 1.

Yield with respect to the converted acetone: 73%.

EXAMPLE 7

A mixture of 3500 g of acetone (60.3 moles), 70 g of ammonium nitrate and 130 g of gaseous ammonia (7.6 moles) is heated for four hours at 60°–65° C.

The mixture is cooled to 20° C., 50 g of NaOH flakes are added, the mixture is stirred for 30 minutes at 20°–25° C. and the aqueous layer is removed.

A solution is obtained containing 810 g of triacetonamine, which is separated from the reaction mixture by distillation. The distilled product (B.P. 75°–78° C./5 mm Hg, B.P. 35°–36° C.) has a purity by gas chromatograph of 99%.

Yield with respect to the converted acetone: 70%.

EXAMPLE 8

A mixture of 3500 g of acetone (60.3 moles), 150 g of granular calcium chloride bihydrate, 50 g of ammonium nitrate and 130 g of gaseous ammonia (7.6 moles) is heated in an autoclave at 80°–85° C. for six hours.

The aqueous layer is removed and the acetone distilled off, and 1000 cc of benzene are added. The solution obtained, containing 857 g of triacetonamine, is washed with a 50% solution of sodium hydrate, dehydrated with anhydrous sodium sulphate, filtered and distilled.

The distilled triacetonamine has a purity measured by gas chromatograph of 98.7%.

Yield with respect to the converted acetone: 73%.

EXAMPLE 9

A mixture of 3500 g of acetone (60.3 moles), 60 g of ammonium nitrate and 150 g of gaseous ammonia (8.8 moles) is heated in an autoclave for six hours at 60°–65° C. After cooling to ambient temperature, 50 g of NaOH flakes are added, the mixture is stirred for 30 minutes at 20°–25° C. and the aqueous layer is separated. The solution obtained contains 833 g of triacetonamine, which is separated as in Example 1.

Yield with respect to the converted acetone: 76%.

EXAMPLE 10

A mixture of 3500 g of acetone (60.3 moles), 70 g of ammonium chloride and 230 g of ammonia (13.5 moles) is heated in an autoclave for six hours at 60°–65° C. After cooling to ambient temperature, 100 g of a 50% aqueous solution of sodium hydrate is added, the mixture stirred for 30 minutes at 20°–25° C., and the aqueous layer removed.

The solution obtained contains 767 g of triacetonamine, which is separated by distillation.

Yield with respect to the converted acetone: 71%.

EXAMPLE 11

A mixture of 3500 g of acetone (60.3 moles), 150 g of granular calcium chloride bihydrate, 50 g of ammonium nitrate and 230 g of gaseous ammonia (13.5 moles) is heated in an autoclave at 80°–85° C. for six hours.

After separating the aqueous layer while hot, the reaction mixture, containing 815 g of triacetonamine, is treated as in Example 1 to separate the triacetonamine in the form of its hydrate.

Yield with respect to the converted acetone: 73%.

EXAMPLE 12

A mixture of 3500 g of acetone (60.3 moles), 150 g of gaseous ammonia (8.8 moles), 150 g $AlCl_3$ is heated to 80° C. for five hours in an autoclave.

After this period, the hot aqueous layer is separated, the unreacted acetone is distilled from the organic layer and the residue is cooled to 0° C. for four hours.

Crystalline triacetonamine hydrate is precipitated and is separated by filtration.

775 g of triacetonamine hydrate are obtained on filtration.

Yield with respect to the converted acetone: 70%.

The process is reproduced in the identical manner while using a molar ratio acetone:ammonia of 3.3:1, which is the maximum ratio used according to the Russian patent. Yield with respect to the converted acetone: 33%.

We claim:

1. In a process for preparing 2,2,6,6-tetramethyl-4-piperidone from ammonia and acetone, in a single stage for a time of 2 to 8 hours, at a temperature of 50° to 120° C. and at a pressure of 1 to 50 atmospheres, in the presence of 0.001–0.1 moles of acid catalysts per mole of acetone, the improvement consisting in reacting the acetone and ammonia in a molar ratio of 20:1 to 4:1.

2. In a process as claimed in claim 1, wherein the acetone to ammonia molar ratio is 10:1 to 4:1.

* * * * *